(12) United States Patent
Cacciaglia et al.

(10) Patent No.: US 6,770,784 B2
(45) Date of Patent: Aug. 3, 2004

(54) USE OF γ-HYDROXYBUTYRIC ACID AMIDES IN THE TREATMENT OF DRUG ADDICTION AND IN PARTICULAR OF ALCOHOLISM

(75) Inventors: Roberto Cacciaglia, Ospedaletti (IT); Antonella Loche, Sanremo (IT); Vincenzo Perlini, Matelica (IT); Lorenza Guano, Sanremo (IT)

(73) Assignee: Laboratorio Farmaceutico C.T. S.r.l., Sanremo (IT)

( * ) Notice: Subject to any disclaimer, the term of this patent is extended or adjusted under 35 U.S.C. 154(b) by 123 days.

(21) Appl. No.: 10/013,971

(22) Filed: Dec. 11, 2001

(65) Prior Publication Data

US 2002/0165224 A1 Nov. 7, 2002

Related U.S. Application Data

(62) Division of application No. 09/242,048, filed as application No. PCT/EP97/04309 on Aug. 7, 1997, now Pat. No. 6,436,998.

(30) Foreign Application Priority Data

Aug. 9, 1996 (IT) .......................................... MI96A1732

(51) Int. Cl.[7] .................... C07C 233/00; C07C 235/00; C07C 237/00; C07C 239/00
(52) U.S. Cl. ........................ 564/202; 564/215; 564/217; 564/218
(58) Field of Search ................................ 564/218, 215, 564/217, 202

(56) References Cited

U.S. PATENT DOCUMENTS 3,940,258 A * 2/1976 Copes .......................... 504/159
5,656,660 A * 8/1997 Lum et al. .................. 514/467

FOREIGN PATENT DOCUMENTS

| EP | 0344704 A1 | * | 12/1989 |
| JP | 54024869 | * | 2/1979 |
| WO | WO93/00083 | * | 1/1993 |

* cited by examiner

*Primary Examiner*—Vickie Kim
(74) *Attorney, Agent, or Firm*—Hedman & Costigan, P.C.

(57) ABSTRACT

Gamma-hydroxybutryic acid amides are used in the treatment of drug addiction and especially in the treatment of alcoholism.

2 Claims, 2 Drawing Sheets

USE OF γ-HYDROXYBUTYRIC ACID AMIDES IN THE TREATMENT OF DRUG ADDICTION AND IN PARTICULAR OF ALCOHOLISM

This application is a DIV of 09/242,048 filed Sep. 2, 1999, now patented U.S. Pat. No. 6,436,998 which is a 371 of PCT/EP 97/4309 filed Aug. 7, 1997.

FIELD OF THE INVENTION

The present invention relates to the use of amides of γ-hydroxybutyric acid, herein referred to as GHB, in the treatment of drug addiction, such as heroine, cocaine and, in particular, in the treatment of alcoholism, and more particularly in reducing chronic alcoholics desire for and habit of consuming alcoholic drinks and in the treatment of abstinence syndrome.

TECHNICAL PROBLEM

The salts of 4-hydroxybutyric acid, e.g. the sodium salt, proved to be effective both in the treatment of the syndrome of abstinence from alcohol and in reducing the desire for and addiction to alcohol in alcoholic patients and disclosed in EP-A-344,704 and in the treatment of drug addiction, as reported in WO 93/00083. One of the advantages of said salts is that they do not cause the inconveniences of Disulfiram (Antabuse®), a drug having several untoward effects, such as for example the symptoms known as the "acetaldehyde syndrome", which may also result in fatality.

The sodium salt of GHB is absorbed very quickly by the gastroenteric apparatus with a maximum concentration peak already at about 35–40 min after administration. However, it presents a half-life time of about 20–25 min, its elimination from the body being rather quick [EP-A-635,265].

In view of the foregoing, to secure a satisfactory pharmacological cover in patients having a craving for alcohol, especially in the early time of treatment, GHB sodium salt has to be administered several times a day, in particular at least 4 times a day.

Therefore, the need for new drugs, active in the treatment of alcoholism, capable of improving the pharmacokinetic aspects of sodium γ-hydroxybutyrate, is deeply felt.

PRIOR ART

U.S. Pat. No. 4,195,096 discloses N-chlorobenzyl-, N-fluorobenzyl- and N-alkyl amides of γ-hydroxybutyric acid as fungicides for plants.

U.S. Pat. No. 3,940,258 describes the use, as aquatic herbicides, of N-phenylalkylamides and in particular the N-benzylamides of GBH, optionally substituted on the phenyl group with methyl or halo groups, useful also as thickeners for lubricants and paints.

N-alkylenebenzoxazinoamides of GHB showing anti-MAO activity are known [J. Heterocyclic Chem., 1983, 20(1), 139–144].

GHB acid amides useful as inflammation and/or allergy inhibitors are N-alkylenebenzenamides of GHB substituted on the benzene ring with alkylene, alkenyl, and alkyleneoxy residues containing hydroxyl groups (Chemical Abstracts, Vol. 112, 1990: CA 112: 55263z relating to JP 01,121,255 [89,121,255]) and an N-alkylenecycloalkylamide of GHB acid described in Chemical Abstracts, Vol. 118, CA 118: 1011592-Eur. J. Med. Chem., 1992, 27(6), 595–610.

U.S. Pat. No. 2,773,062 and U.S. Pat. No. 2,849,455 describe N-α-ethyl-piperonyl ethers of N-benzyl, N-furfuryl, and N-tetrahydrofurfuryl amides of GHB showing insecticidal activity.

Up to the present time no biological activity has been described for the 0-acyl derivatives of GHB amides, such as for example the benzoyl esters of GHB N-benzylamides, useful as components of thermosensitive coating materials [Chemical Abstracts, Calif. 116: 140229; data base abstract referred to JP 3,240,588].

A pharmacological activity has been attributed to imidazoquinolinone-etherified GCIB amides, erg. they are blood-platelet-antiaggregating agents, antiinflammatory agents and/or antithrombotics [Drug Des. Discovery, 1955, 12(3), 249–258].

Chemical Abstract: CA 122:105695 referred to U.S. Pat. No. 957,491 describes the carbostyriloxytocin receptor antagonist activity and the use of GHB carbostyril N-benzylamides as vasodilators and antihypertensives.

Chemical Abstract, Vol. 110, 1989, CA 110: 135655c, referred to EP-A-257,378, describes the antiviral activity of halo-phenyl ethers of a nucleosidic alkylene-pyrimidine amide of GHB.

The body growth stimulation properties of phenoxyamides, e.g. of N-benzylamide of a chlorophenyl ether of GHB, and their use as animal feed additives, have also.

The body growth stimulation properties of phenoxyamides, e.g. of N-benzylamide of a chlorophenyl ether of GHB, and their use as animal feed additives, have also been described [Chemical Abstract, Vol. 104, 1986, p. 607, CA 104:186147x-DD 161,247].

SUMMARY

The applicant has now unexpectedly found that the amides of γ-hydroxybutyric (GHB) acid show a neuropharmacological activity qualitatively comparable to or exceeding that of GHB. If compared to GHB they cause excitatory effects at lower doses and/or of longer duration. Therefore, said amides are useful in the treatment of drug addictions, such as heroin, cocaine and, in particular, in the treatment of alcoholism, and more particularly in reducing chronic alcoholics desire for and habit of consuming alcoholic drinks and in the treatment of abstinence syndrome.

The present invention relates to the use of amides of formula (I)

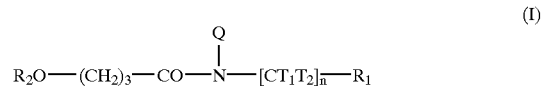

where $R_1$ is a mono- or polycyclic aromatic group, containing one or more carbocyclic or heterocyclic aromatic rings or mixtures thereof, having 5 to 7 atoms in the ring, said rings being optionally substituted with one or more groups selected from $C_1$–$C_8$ alkyl, $C_1$–$C_8$ alkoxyl, one or more aminic monoalkylaminic, dialkyl aminic groups and halogen, where said $C_1$–$C_8$ alkyl and alkoxyl groups may contain or be substituted with one or more double or triple bonds, or with one or more halogen groups and said mono or dialkyl aminic group typically having from 1 to 8 carbon atoms;

$R_2$ is selected from H; a linear or branched alkyl, typically having 1 to 6 carbon atoms; a linear or branched alkyl substituted with one or more double or triple bonds, or with one or more aromatic groups, typically having 1 to 6 carbon atoms;

Q is selected from H and a linear or branched alkyl having 1 to 6 carbon atoms; n is an integer from 1 to 4;

$T_1$ and $T_2$, individually, are selected from H and a linear or branched alkyl having 1 to 6 carbon atoms.

The aforesaid amides are erg. useful in the treatment of alcoholism, and more in particular in reducing the voluntary consumption of ethyl alcohol in alcoholic patients and in the treatment of the abstinence syndrome.

The aforesaid amides are also useful in the treatment of the crises of abstinence from habit-forming drugs, such as heroin, morphine, cocaine, and psychoactive drugs, which are originated from the same biochemical mechanisms as those responsible for the crises of abstinence from alcohol.

To the best of the applicant's knowledge, pharmaceutical compositions containing a therapeutically effective dose of at least an amide of formula (I), in which $R_1$, Q, $T_1$, $T_2$ and n are as defined above, and $R_2$ is selected from the group consisting of H; a linear or branched alkyl, typically having 1 to 6 carbon atoms; a linear or branched alkyl substituted with one or more double or triple bonds or with one or more aromatic groups, typically having 1 to 6 carbon atoms; in combination with one or more pharmaceutically acceptable excipients and/or diluents, have not been described up to the present time.

To the best of the applicant's knowledge, the following amides, the pharmaceutical compositions containing same, and the preparation procedure thereof, have not been described up to the present time and, therefore, constitute further features of the present invention:

a) amides of formula (I), in which $R_1$, Q, $T_1$, $T_2$ and n are as defined above for formula (I), and $R_2$ is selected from the group consisting of a linear or branched alkyl, typically $C_1$–$C_6$; a linear or branched alkyl, typically $C_1$–$C_6$, substituted with one or more double or triple bonds or with one or more aromatic groups;

b) amides of formula (I), in which $R_1$, is an aromatic heterocycle, Q, $T_1$, $T_2$ and n are as defined above for formula (I), and $R_2$ is as defined above for formula (I), provided it is different from an aromatic group, and more particularly $R_2$ is H;

c) amides of formula (I), in which Q is a $C_1$–$C_6$ alkyl, and $R_1$, $R_2$, $T_1$, $T_2$ and n are as defined above for formula (I).

The present invention also relates to the single compounds listed hereinafter, 30 herein referred to as compounds 2), 3), 7) 8), 9), 10), 11), 12), 13), 14)15), 16), 19) (and relevant pharmaceutical compositions and preparation procedure), which, to the applicant's knowledge, are not known to the art [compounds 7), 10), 11), 12), 13), 14), 15), 19) belong to the amides of group a); compound 9) to group b); compound 16) to group c)].

The applicant has also found that the amides of formula (I), in which $R_2$ is alkyl, typically a $C_1$–$C_3$ alkyl, such as methyl, ethyl, and propyl, may be conveniently prepared through the steps of:

a) treating γ-butyrolactone with an alcohol of formula $$R_2OH \qquad (III)$$

in which $R_2$ is an alkyl (preferably $C_1$–$C_3$), in the presence of an ortho-formiate of formula (IV)

$$H—C(OR_2)_3 \qquad (IV)$$

in which $R_2$ is as defined above for the alcohol of formula (III), in the presence of an acid catalyst, to give an ester of formula (V)

$$R_2O—(CH_2)_3—COOR_2 \qquad (V)$$

in which $R_2$ is as defined above for the alcohol of formula (III);

b) treating the ester of formula (V) obtained in a) with an amine of formula (VI)

$$\text{(VI)}$$

where $R_1$, Q, $T_1$, $T_2$, and n are as defined above for formula (I), in the presence of an ammonium halide

DESCRIPTION OF THE DRAWINGS

FIGS. 1 and 2 report the results of the experiment B measuring the effects of the compounds of formula (I) on alcohol consumption (ethanol intake) in Sardinian alcohol preferring rats.

FIG. 2 reports the alcohol intake (g/kg of rat body) of Sardinian alcohol preferring rats treated i.p. respectively with the vehicle (■) and with 100 mg/kg [get—73] 15 minutes before test.

Figure 1A:
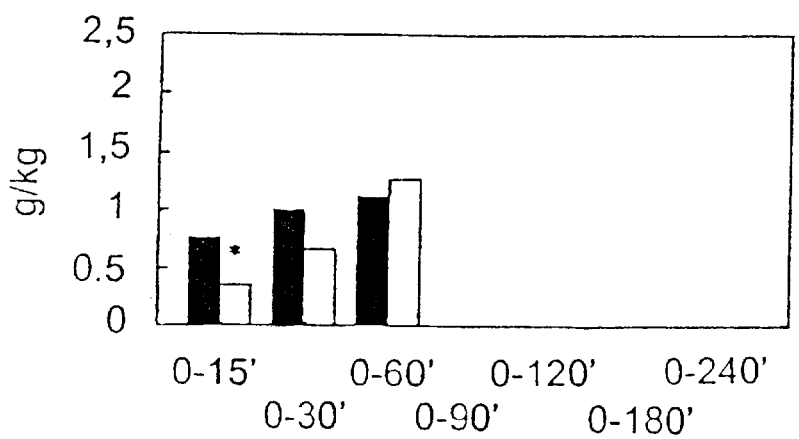
FIG. 1A: reports the alcohol intake (measured as g/kg of rat body) of Sardinian alcohol preferring rats treated i.p. respectively with a physiological solution (saline) (■) and with 300 mg/kg GHB 30 minutes before test (□).

In these figures * means p<0.05;  means p<0.01; * means p<0.005.

DETAILED DESCRIPTION OF THE INVENTION

The following abbreviations are used in the present text: $C_1$–$C_{20}$, $C_1$–$C_8$, $C_1$–$C_6$, $C_1$–$C_3$, and $C_1$–$C_2$. They indicate that the group to which they are referred has 1 to 20, 1 to 8, 1 to 6, 1 to 3 or 1 to 2 carbon atoms, respectively.

When Q, $T_1$ and/or $T_2$ are an alkyl group, they typically have 1 to 3 carbon atoms and are typically methyl. Furthermore, n varies preferably from 1 to 2 and is typically 1.

Typical examples of amides useful in the treatment of alcoholism according to the present invention are the compounds of formula (I), in which Q is H, $T_1$=$T_2$=H and n is 1, i.e. represented by formula (I)A:

$$R_2O—(CH_2)_3—CO—NH—CH_2—R_1 \qquad (I)A$$

in which $R_1$ and $R_2$ are as defined above for formula (I).

In the present text, the aromatic groups present in substituents $R_1$ and $R_2$ are typically represented by a phenyl group or an aromatic heterocycle having 5 or 6 atoms in the ring, and having 1 to 4 heteroatoms selected from N, O and S, optionally substituted or fused with another phenyl group or with another aromatic heterocycle, each phenyl group or aromatic heterocycle being optionally substituted with 1 to 3 substituents as defined above for $R_1$ ($C_1$–$C_8$ alkyl $C_1$–$C_8$ alkoxyl, $C_1$–$C_8$ alkyl substituted with one or more halo groups or halogen).

The aromatic heterocycle is typically attached to the amidic nitrogen through one of its carbon atoms and is, for example, pyridyl, thiophenyl, furanyl.

The substituents of the aromatic group are e.g. alkyl groups having 1 to 3 carbon atoms ($C_1$–$C_3$), such as methyl, ethyl, propyl; $C_1$–$C_3$ alkoxyl groups, such as methoxyl, ethoxyl; $C_1$–$C_3$ alkyl groups substituted with 1 to 3 halogens, such as trifluoromethyl, and halogens, typically chlorine, aminic groups, $C_1$–$C_3$ mono- or dialkyl amminic groups.

$R_1$ is preferably an aromatic group as defined above and, more particularly, phenyl, a phenyl substituted as specified above for $R_1$, naphthyl, or an aromatic heterocycle having 1 heteroatom, in particular phenyl, 1-naphthyl, 4-methylphenyl, 4-methoxyphenyl, 4-amino-phenyl, 3,5-dimethoxyphenyl, 4-chlorophenyl, 4-trifluoromethyl, 3-pyridyl, 2-thiophenyl.

According to typical embodiments of the present invention, $R_2$ is H, $C_1$–$C_6$ alkyl, in particular saturated and unsubstituted, e.g. methyl, ethyl, n-propyl.

According to a preferred embodiment of the present invention, $R_2$ is alkyl (typically saturated and unsubstituted) having 1 to 3 carbon atoms, more preferably methyl.

According to a further preferred embodiment of the present invention, $R_2$ is $C_1$–$C_3$ alkyl substituted with 1 to 3 aromatic groups, typically phenyl, and is selected more preferably from —$CH_2Ph$, —$CH(Ph)_2$ and —$C(Ph)_3$ [Ph= phenyl].

Typical embodiments of the present invention are the amides of formula (I), and more particularly of formula (I)A, in which $R_1$ is phenyl or a phenyl substituted with at least one group selected from $C_1$–$C_3$ alkyl, $C_1$–$C_3$ trihaloalkyl and halogen, and $R_2$ is H, $C_1$–$C_3$ alkyl, typically unsubstituted.

The applicant has also surprisingly found that the presence of a substituent, in particular a $C_1$–$C_2$ alkyl, on the hydroxyl of the γ-hydroxybutyric skeleton can increase its potency and/or duration of action, said effect being more remarkable when said substituent is a methyl group, and that in the amides in which $R_1$ is phenyl, the potency and/or duration of action are increased in the presence of at least a substituent on the aromatic ring. Potency and duration of action are increased to a greater extent in the compounds characterised by the presence of substituents different from H on the hydroxyl and on the benzene ring.

Therefore, preferred amides are the ones of formula (I), and more particularly of formula (I)A, in which $R_2$ is $C_1$–$C_2$ alkyl, more preferably methyl, and, out of them, those of formula (I) or (I)A, in which $R_1$ is phenyl or a phenyl substituted with at least a substituent selected from $C_1$–$C_3$ alkyl, $C_1$–$C_3$ trihaloalkyl, halogen, aminic, $C_1$–$C_3$ mono- or dialkyl aminic groups.

Typically, the phenyl is substituted with a substituent in para position, in particular with an alkyl (such as methyl) or a halogen (such as chlorine), more preferably an alkyl (methyl).

Exemplary amides useful for the purposes of the present invention are the amides of formula (I) corresponding to compounds 1) through 9) as defined in Table 1 reported hereinafter.

In view of the foregoing, the preferred compounds among those listed above are the amides of formula (I)A [compounds 1) through 15)] and particularly preferred are the ones in which $R_1$ is selected from phenyl, 4-methylphenyl and 4-trifluoromethyl, 1-naphthyl and $R_2$ is selected from H, methyl, ethyl, n-propyl, such as compounds 5), 7), 10), 12), 13), 14) and 15) reported above.

Still particularly preferred are the amides in which $R_1$ is a substituted phenyl and $R_2$ is methyl, such as compounds 5), 7) 14) and 15).

The amides of formula (I), several of which are already known, can be prepared by methods described herein or by different methods known in the literature.

For example, the amides of formula (I), in which $R_2$ is H, represented by formula (I)B

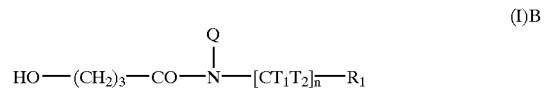

(I)B in which $R_1$, Q, $T_1$, $T_2$ and n are as defined for formula (I) in the Summary or elsewhere in the present text, are prepared by reacting γ-butyrolactone with the corresponding amine of formula (II)

(II)

in which $R_1$, Q, $T_1$, $T_2$ and n are as defined above.

The present invention also includes the illustrated process for the preparation of the amides of formula (I), in which $R_1$ is an aromatic heterocycle, $R_2$ is H, and Q, $T_1$, $T_2$ and n are as defined for formula (I) in the Summary or elsewhere in the present text.

Under typical operating conditions, the reaction is carried out by contacting almost equimolar amounts of reagents in the absence of solvent. The temperature generally ranges from 100° C. to 200° C., preferably from 130° C. to 160° C. Generally, when the amine of formula (II) is liquid or solid or in any case poorly volatile (e.g., when $R_1$ is an aromatic heterocycle) the reaction proceeds at atmospheric pressure for approximately 8 to 16 h; when the amine is volatile or gaseous, as is the case of ethylamine, the reaction is preferably carried out at a pressure above the atmospheric, e.g. in a bomb, for a period of approximately 1 to 5 h.

In the described synthesis of the amides of formula (I), in which $R_2$ is an alkyl, in particular methyl, ethyl or propyl, step a) is typically carried out by reacting γ-butyrolactone with the corresponding ortho-formiate of formula $HC(OR_2)_3$, generally in an amount of 1.5–2 mol per mol γ-butyrolactone, using the alcohol of formula (III) $R_2OH$ as the solvent, if in the liquid state.

The acid catalyst used is typically an inorganic acid (e.g. hydrochloric acid, sulphuric acid), generally in a quantity of 0.05 to 0.5 equivalent in respect of γ-butyrolactone, such as for example 0.1 equivalent sulphuric acid.

The reaction temperature generally ranges from approximately 30° C. to 100° C., preferably from approximately 50° C. to 80° C.

The ester of formula (V) is typically isolated from the reaction mixture by extraction with an organic solvent (e.g. ethyl acetate), followed by distillation under reduced pressure to remove unreacted products.

Step b) is carried out by causing the ester of formula (V) to react with the amine of formula (VI), in the presence of a catalyst consisting of ammonium salt, generally in the absence of solvent, at a temperature generally ranging from approximately 100° C. to 200° C., preferably from approximately 160° C. to 170° C., preferably in a bomb at a pressure ranging from atmospheric to autogenous pressure.

Ammonium halide is used in a quantity ranging erg. from 0.01 to 0.1 equiv. in respect of the substrate (ester or amine) and is typically $NH_4Cl$.

In the syntheses described above, the amides of formula (I) or the intermediates, if any, are isolated by conventional techniques and purified e.g. by silica or Florisil chromatography, optionally followed by crystallization, as reported e.g. in the experimental examples.

In human therapy, the amides of formula (I) may be administered, in combination with pharmaceutically acceptable excipients and/or diluents, as conventional pharmaceutical compositions, by the oral or parenteral way.

The excipients selected depend not only on the physicochemical characteristics of the active ingredient, but also on the desired composition and on the required dosage.

The compositions according to the present invention contain e.g. from 12.5% to approximately 50% by weight of an amide of γ-hydroxybutyric acid.

For the purposes of the present invention, the amides of γ-hydroxybutyric acid of formula (I) may be administered to man at dosage rates ranging approximately from 5 mg to 50 mg/kg/die (mg per kg body/weight per day) as well as at different, in particular lower, dosage rates, depending on the potency of the single amide and/or on the patient's state.

For example, the pharmaceutical compositions for oral or parenteral administration may be in the solid form, such as powders, granules, compressed tablets, optionally effervescent, sachets, hard or soft capsules, pills, or in the liquid form, such as solutions, suspensions or emulsions, to be administered e.g. by the oral way (e.g. drops or syrups) or for injection, e.g. solutions or compositions in vials.

In solid compositions (e.g. tablets), the solid amides of formula (I) may be combined with solid excipients, such as silica, magnesium stearate or other excipients for tablets (lubricants, disgregating agents, etc.).

In liquid compositions, the solvents and/or diluents used may be water mixtures (e.g. water for injection) and organic solvents, such as dimethylformamide and dimethylsulphoxide, in concentrations ranging from approximately 20% to 60%, alcohols, such as ethanol and methanol.

Liquid preparations may also contain emulsifiers or dispersants, e.g. fatty acids or salts thereof, or other surfactants.

When the amides of formula (I) and, in particular, of formula (I)A, in which $R_1$ is phenyl or a phenyl susbtituted with $C_1-C_8$ alkyl, $C_1-C_8$ alkyl substituted with 1 to 3 halogen groups, $C_1-C_8$ alkoxyl, halogen, amminic, $C_1-C_8$ mono- or dialkylamminic groups the other substituents being as defined above, are formulated as powders or solid granules, or as liquid formulations (solutions, suspensions, emulsions), their concentration is generally higher than 0.25% by volume or by weight in respect of the final composition (e.g. from 12.5% to 60%), and typically higher than 25% by volume or by weight.

The following examples are conveyed by way of indication, not of limitation, of the present invention.

Table 1:

Products 1) through 19) of formula (I), in which substituents $R_1$, $T_1$, $T_2$, n, Q, and $R_2$ have the meanings reported in the table below, have been synthesized.

TABLE 1

Products synthesized $$R_2O-(CH_2)_3-CO-\underset{\underset{Q}{|}}{N}-[CT_1T_2]_{\overline{n}}-R_1 \quad (I)$$

| Product | $R_1$ | $T_1$ | $T_2$ | n | Q | $R_2$ |
|---|---|---|---|---|---|---|
| 1) | phenyl | H | H | 1 | H | H |
| 2) | ethyl | H | H | 1 | H | H |
| 3) | 4-aminophenyl | H | H | 1 | H | H |
| 4) | 4-chlorophenyl | H | H | 1 | H | H |
| 5) | 4-methylphenyl | H | H | 1 | H | H |
| 6) | 4-methoxyphenyl | H | H | 1 | H | H |
| 7) | 4-methylphenyl | H | H | 1 | H | $CH_3-$ |
| 8) | 3,5-dimethoxyphenyl | H | H | 1 | H | H |
| 9) | 3-pyridyl | H | H | 1 | H | H |
| 10) | phenyl | H | H | I | H | $CH_3-$ |
| 11) | 4-chlorophenyl | H | H | 1 | H | $CH_3-$ |
| 12) | 4-methylphenyl | H | H | 1 | H | $CH_3CH_2-$ |
| 13) | 4-methylphenyl | H | H | 1 | H | $n-C_3H_7-$ |
| 14) | 1-naphthyl | H | H | 1 | H | $CH_3-$ |
| 15) | 4-($CF_3$)-phenyl | H | H | 1 | H | $CH_3$ |
| 16) | phenyl | H | H | 1 | $CH_3-$ | H |
| 17) | phenyl | H | H | 2 | H | H |
| 18) | phenyl | H | $CH_3$ | 1 | H | H |
| 19) | 4-amino-phenyl | H | H | 1 | H | $CH_3$ |

4-($CF_3$) = 4-trifluoromethyl; $n-C_3H_6 = CH_3CH_2CH_2-$ 4-($CF_3$)=4-trifluoromethyl; $n-C_3H_7=CH_3CH_2CH_2-$ I) Synthesis of Compound 2):

An equimolar mixture of γ-butyrolactone and anhydrous ethylamine was heated in a bomb to 130° C. for 3 h. After cooling, the residue was purified by silica gel chromatography, with $CH_2Cl_2-CH_3OH$, 9/1.

II) General Method of Synthesis of Compounds 1), 3), 4), 5), 6), 8), 9), 16), 17), and 18)

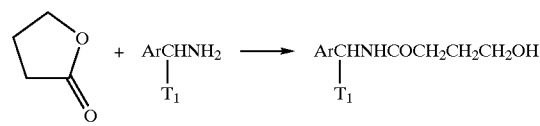

where Ar is as defined in Table 1 for $R_1$, and $T_1$ is H or $CH_3$.

γ-Butyrolactone and a suitable amine in equimolar amounts were mixed without solvent addition, heated slowly to approximately. 130° C. to 160° C., while the reaction was controlled by TLC (ethyl acetate-cyclohexane, 4/6). The reaction was usually completed in 8 to 16 h. In compounds 3), 4), 5), 6), and 17), the desired product precipitated directly from the reaction mixture by cooling and optional addition of diisopropyl ether. Filtration and recrystallization were performed [compound 1): $CH_2Cl_2/ET_2O$; compound 4): $CH_2Cl_2$; compound 5): duisopropyl ether/$Et_2O$; compound 6): $CH_2Cl_2$/diisopropyl ether; compound 17): $CH_2Cl_2$/diisopropyl ether].

As concerns compound 16), the unreacted starting products were eliminated from the reaction mixture by distillation (10 mmHg). The crude was purified by silica gel chromatography eluting with cyclohexane gradient 100 parts up to reaching cycloexane/ethylacetate 100:100, yielding an oily product (isomeric mixture: cf. $^1H-NMR$).

As concerns compounds 8), 9), and 18), the reaction mixture was directly chromatographed on silica eluting with $CH_2Cl_2-MeOH$, 100/1.

III) General Method of Synthesis of Compounds 7), 10), 11), 12), 13), 14), 15) and 19)

A) Preparation of 4-Alkoxybutyric Acid Ester:

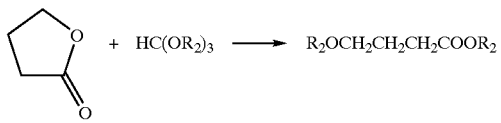

where $R_2=CH_3$; $C_2H_5$, $C_3H_7$.

1 equivalent lactone was mixed with 1.5–2 equivalent ortho-formiate in the corresponding alcohol as solvent, in the presence of 0.1 equivalent sulphuric acid. The mixture was heated to 50–80° C. for 8 h. The solvent was evaporated under reduced pressure and the residue was washed with a saturated bicarbonate solution. The product was extracted with ethyl acetate. The separated and anhydrified organic phase was distilled under reduced pressure. Overheads, generally consisting of unreacted starting materials, were removed, and the desired ester was collected.

B) Reaction of 4-Alkoxybutyric Ester with Amines

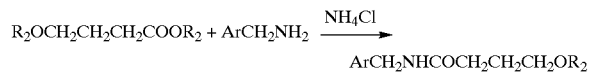

The ester synthesized according to the preceding method and a suitable amine in equimolar amounts, plus $NH_4Cl$ in a catalytic amount, were mixed and heated in a bomb to 160–170° C. The reaction was controlled by TLC (ethyl acetate-cyclohexane, 7/3). The mixture was dissolved in methanol and evaporated to dryness. The crude obtained was chromatographed on silica gel eluting in gradient up to reaching cycloexane/ethylacetate 100:1000). The products obtained were crystallized from $CH_2Cl_2/Et_2O$.

Analytical and Spectroscopic Data

Compound 1) [Get—29]: M.p. 70–72° C.
Elemental Analysis
Calculated for $C_{11}H_{15}NO_2$: C, 68.39%; H, 7.77%; N. 7.25%. Found: C, 68.04%; H, 7.75%; N, 7.27%. $^1H$—NMR ($CDCl_3$): 1.80–2.00 (m, 2H); 2.35 (t, J=7.0, 2H); 3.15 (bs, 1H deut., OH); 3.65 (t, J=5.5, 2H); 4.40 (d, J=5.5, 2H); 6.20 (bs, 1 H deut., NH); 7.20–7.40 (m, 5H, aryl-H).

Compound 2) [Get—30]: M.p.: Oil.
Elemental Analysis
Calculated for $C_6H_{13}NO_2$: C, 54.96%; H, 9.92%; N, 10.69%. Found: C, 54.64%; H, 9.75%; N, 10.27%, $^1H$—NMR ($CDCl_3$): 1.10 (t, J=7.0, 3H); 1.75 (m, 2H); 2.28 (t, J=7.0, 2H); 3.15 (m, 2H); 3.60 (t, J=5.5, 2Hf); 4.20 (bs, 1H deut., OH); 6.60 (bs, 1H deut., NH).

Compound 3) [Get—80]: M.p.: 68–70° C.
Elemental Analvsis
Calculated for $C_{11}H_{16}NO_2$: C, 63.46%; H, 7.64%; N, 13.46%. Found: C, 63.11%; H, 7.85%; N,13.19%.

Compound 16) [Get—54]: M.p.: Oil.
Elemental Analysis
Calculated for $C_{12}H_{17}NO_2$: C, 69.56%; H, 8.21%; N, 6.76%. Found: C, 69.04%; H, 8.01%; N, 6.57%. $^1H$—NMR ($CDCl_3$): 1.80–2.00 (m, 2H); 2.55 (t, J=7.0, 2H); 2.95 (m, 2H); 3.50 (bs, 1H deut., OH); 3.70 (m, 2H); 4.55 (d, J=7.0, 2H); 7.10–7.40 (m, 5H, aryl-H).

Compound 4) [Get—56]: M.p.: 86–87° C.
Elemental Analysis
Calculated for $C_{11}H_{14}ClNO_2$: C, 58.02%; H, 6.15%; N, 6.15%. Found: C, 57.98%; H, 5.99%; N, 5.97%. $^1H$—NMR ($CDCl_3$): 1.80–2.00 (m, 2H); 2.40 (t, J=7.0, 2H); 2.70 (bs, 1H deut., OH); 3.70 (t, J=5.5, 2H); 4.40 (d, J=6.0, 2H); 6.05 (bs, 1H deut., NH); 7.20–7.40 (m, 4H, aryl-H).

Compound 5) [Get—57]: M.p.: 72° C.
Elemental Analysis
Calculated for $C_{12}H_{17}NO_2$: C, 69.56%; H, 8.21%; N, 6.76%. Found: C, 69.06%; H, 6.56%; N, 5.97%. $^1H$—NMR ($CDCl_3$): 1.80–2.00 (m, 2H); 2.30–2.50 (m, 5H); 2.90 (bs, 1H deut., OH); 3.70 (m, 2H); 4.40 (d, J=5.5, 2H); 5.95 (bs, 1H deut., NH); 7.10–7.25 (m, 4H, aryl-H).

Compound 6) [Get—60]: M.p.: 101° C.
Elemental Analysis
Calculated for $C_{12}H_{17}NO_3$: C, 64.57%; H, 7.62%; N, 6.28%. Found: C, 64.07%; H, 7.56%; N, 5.97%. $^1H$—NMR ($CDCl_3$): 1.80–2.00 (m, 2H); 2.40 (t, J=6.5, 2H); 2.90 (bs, 1H deut., OH); 3.69 (t, J=5.5, 2H); 3.75 (s, 3H); 4.36 (d, J=5.5, 2H); 5.95 (bs, 1H deut., NH); 6.95 (d, J=8.5, 2H, aryl-H); 7.20 (d, J=8.0, 2H, aryl-H).

Compound 17) [Get—61]: M.p.: 52° C.
Elemental Analysis
Calculated for $C_{12}H_{17}NO_2$: C, 69.56%; H, 8.21%; N. 6.76%. Found: C, 69.19%; H. 7.98%; N, 6.38%. $^1H$—NMR ($CDCl_3$): 1.70–1.90 (m, 2H); 2.28 (t, J=6.5, 2H); 2.80 (t, J=7.0, 2H); 3.35 (bs, 1H deut., OH); 3.40–3.70 (m, 4H); 6.00 (bs, 1 H deut., NH); 7.10–7.40 (m, 5H, aryl-H).

Compound 7) [Get 63]: M.p: 59–60° C.
Elemental Analysis
Calculated for $C_{13}H_{19}NO_2$: C, 70.59%; H, 8.60%; N, 6.33%. Found: C, 70.19%; H, 8.25%; N, 6.01%. $^1H$—NMR ($CDCl_3$): 1.80–2.00 (m, 2H); 2.20–2.40 (m, 5H); 3.25 (s, 3H); 3.40 (t, J=6.0, 2H); 4.39 (d, J=5.5, 2H); 6.10 (bs, 1H deut., NH); 7.10–7.20 (m, 4H, aryl-H).

Compound 8) [Get—64]: M.p.: 52° C.
Elemental Analysis
Calculated for $C_{13}H_{19}NO_4$: C, 61.66%; H, 7.51%; N, 5.53%. Found: C, 61.51%; H, 7.25%; N, 5.16%. $^1H$—NMR ($CDCl_3$): 1.80–2.00 (m, 2H); 2.40 (t, J=7.0, 2H); 2.95(bs, 1H deut., NH); 3.60–3.75 (m, 2H); 3.80 (s, 6H); 4.35 (d, J=5.5, 2H); 6.10 (bs, 1H deut., NH); 6.30–6.50 (m, 3H, aryl-H).

Compound 9) [Get 65]: M.p.: Oil.
Elemental Analysis
Calculated for $C_{10}H_{14}N_2O_2$: C, 61.85%; H, 7.22%; N, 14.43%. Found: C, 61.51%; H, 7.01%; N, 14.16%. $^1H$—NMR (DMSO): 1.60–1.80 (m, 2H); 2.20 (t, J=8.0, 2H); 4.30 (d, J=6.0, 2H); 4.50 (bs, 1H deut., OH); 7.30–7.40 (m, 1H, aryl-H); 7.60–7.70 (m, 1H, aryl-H); 8.15–8.25 (m, 3H, aryl-H+NH).

Compound 18) [Get—66]: M.p.: Oil.
Elemental Analysis
Calculated for $C_{12}H_{17}NO_2$: C, 69.56%; H, 8.21%; N, 6.76%. Found: C, 69.51%; H, 8.01%; N, 6.26%. $^1H$—NMR ($CDCl_3$): 1.45 (d, J=7.0, 3H); 1.70–1.90 (m, 2H); 2.30 (t, J=6.5, 2H); 2.80 (bs, 1H deut., OH); 3.62 (t, J=6.0, 2H); 5.00–5.20 (m, 1H); 6.10 (bs, 1H deut., NH); 7.20–7.40 (m, 5H, aryl-H).

Compound 10) [Get 67]: M.p.: Oil.
Elemental Analysis
Calculated for $C_2H_{17}NO_2$: C, 69.56%; H, 8.21%; N, 6.76%. Found: C, 68.11%; H, 7.98%; N, 6.37%. $^1H$—NMR ($CDCl_3$): 1.80–2.00 (m, 2H); 2.31 (t, J=7.0, 2H); 3.30 (s, 3H); 3.41 (t, J=6.0, 2H); 4.43 (d, J=5.5, 2H); 6.10 (bs, 1H deut., NH); 7.20–7.40 (m, 5H, aryl-H).

Compound 11) [Get—68]: M.p.: 67–68° C.
Elemental Analysis
Calculated for $C_{12}H_{16}ClNO_2$: C, 59.63%; H, 6.62%; N, 5.80%. Found: C, 59.31%; H, 6.38%; N, 5.57%. $^1H$—NMR ($CDCl_3$): 1.85–2.00 (m, 2H); 2.35 (t, J=7.0, 2H); 3.30 (s, 3H); 3.42 (t, J=6.0, 2H); 4.40 (d, J=5.5, 2H); 6.10 (bs, 1H deut., NH); 7.20–7.40 (m, 4H, aryl-H).

Compound 12) [Get 69]: M.p.: 71–72° C.
Elemental Analysis
Calculated for $C_{15}H_{23}NO_2$: C, 71.49%; H, 8.94%; N, 5.96%. Found: C, 71.19%; H, 8.64%; N, 5.56%. $^1$H—NMR ($CDCl_3$): 1.10 (t, J=7.0, 3H); 1.78–1.81 (m, 2H); 2.20–2.35 (m, 2H); 3.30–3.50 (m, 4H); 4.30 (d, J=5.5, 2H); 6.10 (bs, 1H deut., NH); 7.10–7.20 (m, 4H, aryl-H).
Compound 13) [Get—70]: M.p.: 39–40° C.
Elemental Analysis
Calculated for $C_{14}H_{21}NO_2$: C, 72.29%; H, 9.24%; N, 5.62%. Found: C, 72.09%; H. 9.04%; N, 5.46%. $^1$H—NMR ($CDCl_3$): 0.85 (t, J=7.0, 3H); 1.41–1.55 (m, 2H); 1.86–1.96 (m, 2H); 2.27–2.33 (m, 3H); 3.31 (t, J=7.0, 2H); 3.42 (t, J=6.0, 2H); 4.36 (d, J=5.5, 2H); 6.10 (bs, 1H deut., NH); 7.08–7.18 (m, 4H, aryl-H).
Compound 14) [Get 72]: M.p.: 89° C.
Elemental Analysis
Calculated for $C_{16}H_{19}NO_2$: C, 74.71%; H, 7.39%; N, 5.45%. Found: C, 74.52%; H, 7.08%; N, 5.26%. $^1$H—NMR ($CDCl_3$): 1.85–1.98 (m, 2H); 2.30 (t, J=7.0, 2H); 3.18 (s, 3H); 3.37 (t, J=6.0, 2H); 4.89 (d, J=5.0, 2H); 5.97 (bs, 1H deut., NH); 7.38–8.04 (m, 7H, aryl-H).
Compound 15) [Get—73]: M.p.: 73° C.
Elemental Analysis
Calculated for $C_{13}H_{16}F_3NO_2$: C, 56.72%; H, 5.82%; N, 5.09%. Found: C, 56.53%; H, 5.42%; N, 4.97%. $^1$H—NMR ($CDCl_3$): 1.87–2.00 (m, 2H); 2.36 (t, H=7.0, 2H); 3.30 (s, 3H); 3.42 (t, J=6.0, 2H); 4.50 (d, J=6.0, 2H); 6.22 (bs, 1H deut., NH); 7.39 (d, J=8.0, 2H, aryl-H); 7.59 (d, J=8.0, 2H, aryl-H).

Pharmacological Tests

A) Neuropharmacological Profile

The tests, which were intended to evaluate the neuropharmacological activity of the amides of the invention, were conducted on rats, because most of the data available in the literature concern said animal species.

Each compound was administered by intraperitoneal route at different dosage levels; treated animals were placed in a box (50×50×30 cm) and their behaviour was observed at regular intervals.

The time at which the effects started, their intensity and duration were recorded.

The compounds assayed [Nos. 3), 5), 7), 10), 11), 12), 13), 14) and 15)] showed a biphasic neuropharmacological profile, qualitatively comparable to that of GHB, which causes excitation at relatively low doses and sedation at higher doses. Molecules were evaluated by systematically using a control group, in which rats had been treated with the utilized solvent, and a positive control group, in which rats had been treated intraperitoneally (i.p.) with a standard dose of GHB sodium salt (100 mg/kg) in 2 ml. GHB and the assayed amides were administered in 50% DMSO in distilled water.

Said dose of drug, used as a reference, produced typical excitatory effects, characterized by the onset of generic excitation accompanied by more particular paroxysms, the so-called BURSTS of excitation.

Generic excitation was characterized by an increased motor activity, extremely sharp and jerky movements, higher reactivity and shakes.

"Bursts" of excitation were typical and well recognizable: the animals fought and frantically pursued each other.

Recordings concerned the number of "bursts", the time of their onset after treatment, their intensity, the partial or total involvement of treated animals, the duration of the single episodes.

The sedation produced by higher doses of the molecules examined was evaluated analogously: time of onset, degree of sedation, partial or total involvement, duration of the effects.

On the basis of said recordings, the profile of pharmacological activity of the tested compounds proved to be qualitatively comparable to that of GHB; furthermore, and it was possible to give a first indication about their relative potency and duration of action could be evaluated.

Utilizing these preliminary goods results, the effects of said compounds were studied on the rats motor activity. This experiment permits to obtain a more objective evaluation about the effectiveness of the tested molecules, confirming and specifying the effective dosages, start and duration of the effects.

For these tests too, rats were subdvided into two groups: a control group of rats treated with the solvent and a positive control group consisting of rats treated i.p. with 300 mg/kg/2 ml GHB sodium salt in the aforesaid solvent.

GHB was systematically used as a reference: when administered at the above doses its motor reducing action spans a wide variation range.

Results

The derivatives indicated herein as compounds 3), 4), 5), 6), 7), 8), 9), 10), 11), 12), 13), 14) and 15) have been assayed.

A.1) General Neuropharmacological Profile

The results are recapitulated in the following table.
Table 2—General Neuropharmacological Profile of Benzylamido Derivatives of GHB Compared With a 100 mq/kg Dose of GHB (Excitatory Dose)

TABLE 2

Structure of the assayed amides:

$R_2O—(CH_2)_3—CO—NH—R_1$ (I)

| | | | Dose | Excitatory effects | |
|---|---|---|---|---|---|
| Ref. | $R_1$ | $R_2$ | mg/kg | Start | Duration |
| 5) [get 57] | 4-methyl-phenyl | H | 100 | 20 min | 1 h 30 min |
| 7) [get-63] | 4-methyl-phenyl | —$CH_3$ | 25–50 | 20 min | 2 h 30 min |
| 10) [get-67] | phenyl | —$CH_3$ | 25–50 | 20 min | 30 min |
| 11) [get-68] | 4-cloro-phenyl | —$CH_3$ | 25–50 | 20 min | 1 h |
| 12) [get-69] | 4-metyl-phenyl | —$CH_2CH_3$ | 25–50 | 1 h | 30 min |
| 13) [get-70] | 4-metyl phenyl | —$CH_2CH_2CH_3$ | 100 | 45 min | 30 min |
| 14) [get-72] | 1-napthyl | —$CH_3$ | 25–50 | 30 min | 3 h |
| 15) [get-73] | 4-$CF_3$-phenyl | —$CH_3$ | 25–50 | 20 min | 3 h 30 min |
| 8) [get-64] | 3,5-dimeth-oxy-phenyl | H | 100 | 1 h | 30 min |
| 9) [get-65] | 3-pyridyl | H | 100 | 1 h | 15 min |
| 6) [get-60] | 4-meth-oxy-phenyl | H | 25–50 | 45 min | 45 min |
| 4) [get-65] | 4-chloro phenyl | H | 50–100 | 30 min | 45 min |
| 3) [get-80] | 4-amino phenyl | H | 25–50 | 30 min | 1 h |

All molecules listed above showed a GHB-similar profile and a fully satisfactory neuropharmacological activity.

Compound 5) is substantially superimposable to GHB acid both in terms of dose (100 mg/kg) and of duration of action.

Compounds 3), 7), 10),11), 12), 14) and 15) are more powerful than GHB, a lower dosage of them (25–50 mg/kg) being required; out of them, compounds 7), 14) and 15) show longer duration of action.

Compounds 7), 14) and 15) exhibit the best properties: compared with GHB, they induce—at lower doses—substantial and typical excitatory effects and shows longer duration of action (approximately 2 h and 30 min, 3 h and 30 minutes versus 1 h of GHB).

A.2) Effects on the Motor Activity of the Rat

Table 3—Effects on the Motor Activity Produced by Some Benzylamido Derivatives of GHB Compared With a 300 mg/kg Dose of GHB (Sedative Dose)

The following table reports data referred to the first half hour after administration. The per cent decreases in motor activity in respect of GHB are reported.

TABLE 3

9/24 Structure of the assayed amides:
$R_2O-(CH_2)_3-CO-NH-CH_2-R_1$ (I)
$R_2$

| Ref. | $R_1$ | $R_2$ | Dose mg/kg | < % |
|---|---|---|---|---|
| 10) [get-67] | phenyl | —CH$_3$ | 100 | 42 |
| 7) [get-63] | 4-methoxy-phenyl | —CH$_3$ | 100 | 76 |
| 11) [get-68] | 4-cloro-phenyl | —CH$_3$ | 100 | 70 |
| 12) [get-69] | 4-methyl-phenyl | —CH$_2$CH$_3$ | 100 | 54.5 |
| 13) [get-70] | 4-methyl-phenyl | —CH$_2$CH$_2$CH$_3$ | 100 | 58 |
| 5) [get-57] | 4-methyl-phenyl | H | 300 | 77 |
| 9) [get-65] | 3-pyridyl | H | 100–200 | 0 |
|  |  |  | 300 | 72 |
| 14) [get-72] | 1-naphthyl | —CH$_3$ | 50 | 65 |
|  |  |  | 100 | 75 |
| 1) [get-24] | phenyl | H |  |  |
| 4) [get-56] | 4-chloro-phenyl | H | 100 | 0 |
|  |  |  | 300 | 80 |
| 6) [get-60] | 4-methoxy-phenyl | H | 300 | 57 |
| 8) [get-64] | 3,5-dimethoxy-phenyl | H | 300 | 68 |
| 2) [get-80] | 4-amino-phenyl | H | 300 | 82 |
| 15) [get-73] | 4-trifluoro-methyl | —CH$_3$ | 25–50 | 64 |

CONCLUSIONS

The results obtained so far surprisingly show that the activity of all assayed amides is qualitatively comparable to that of GHB and quantitatively satisfactory. As may be inferred from the comparison of the results obtained with compounds 5) [get—57], 7) [get—63], 10) [get—67], 11) [get—68], 14) [get—72] and 15) [get—73] the potency of benzylamido derivatives is increased by the presence of substituents on the hydroxyl and on the aromatic ring. However, the extension of the aliphatic chain on the hydroxyl when passing from methyl to higher homologues does not produce any further increase in activity [cf. compounds 12) and 13)].

On the basis of the results obtained so far, compound 7), 14) and 15) exhibit properties of potency and duration of action that are better than those of GHB.

B. Effects of the Compounds of Formula (I) on Alcohol Consumption in Sardinian Alcohol Preferring Rats On the base of the results of the previous experiments, it was possible to select four benzylamide derivatives of GHB, having a biphasic profile analogous to that of GHB, and able to induce sedative effects to reduce considerably the motor activity of the rat after treatment with equal doses [get—57] or higher than that usually encompassed for GHB (300 mg/kg i.p.).

These four compounds are:
Compound 5) [get—57]
Compound 7) [get—63]
Compound 14) [get—72]
Compound 15) [get—73].

For this study male rats were used of the line sP (selected for the spontaneous alcohol consumption) 6–9 months old, individually stalled under light-dark inverted cycle conditions (on:21–9).

The rats could choose between a 10% v/v alcoholic solution and water, this regime of free choice was limited to 4 hours from 9 a.m. to 1 p.m.

During the remaining 20 hours only water and food was available at libitum, and the alcohol and water consumption were recorded at regular intervals: 15, 30, 60, 90, 120, 180, 240 minutes after bottle submission.

The tested compounds were administered i.p. 15 minutes before bottle submission.

The control groups were i.p. treated only with the vehicle used for dissolving tested compounds, and in the same injection volume.

Figure 1B:
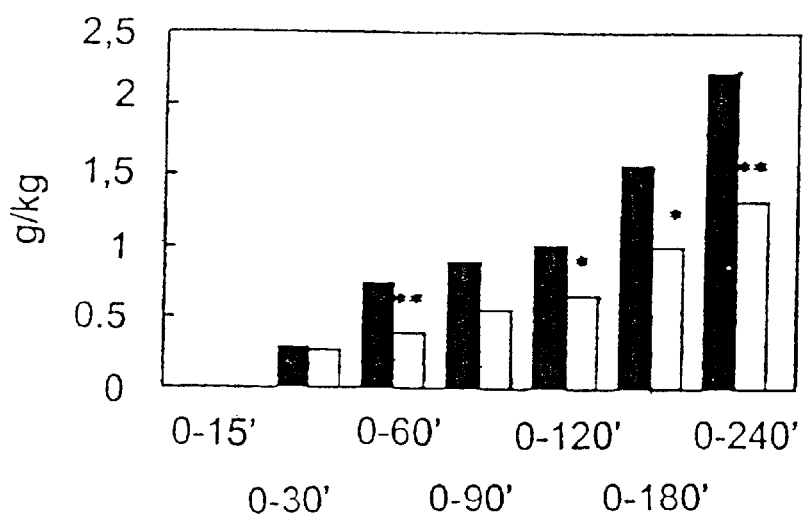
FIG. 1B: reports the alcohol intake (g/kg of rat body) of Sardinian alcohol preferring rats treated i.p. respectively with the vehicle (■) and [get—57] 15 minutes before test (□).
Figure 1C:
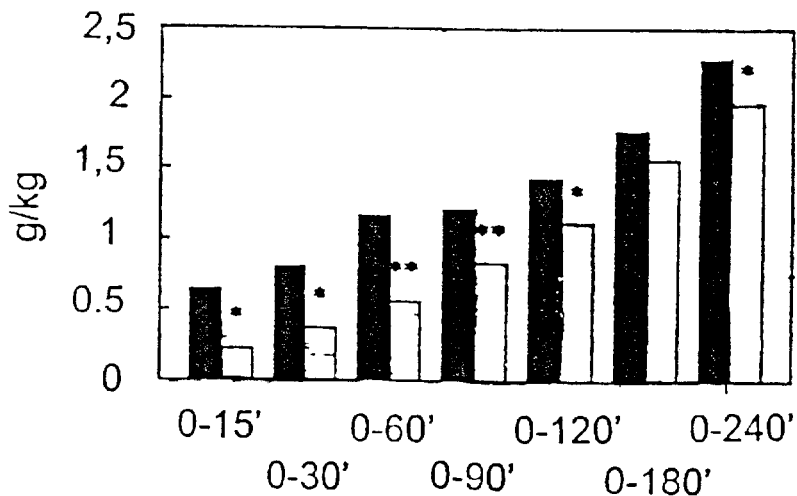
FIG. 1C reports the alcohol intake (g/kg of rat body) of Sardinian alcohol preferring rats treated i.p. respectively with the vehicle (■) and with [get—63] 200 mg/kg i.p. 15 minutes before test (□).
Figure 2:
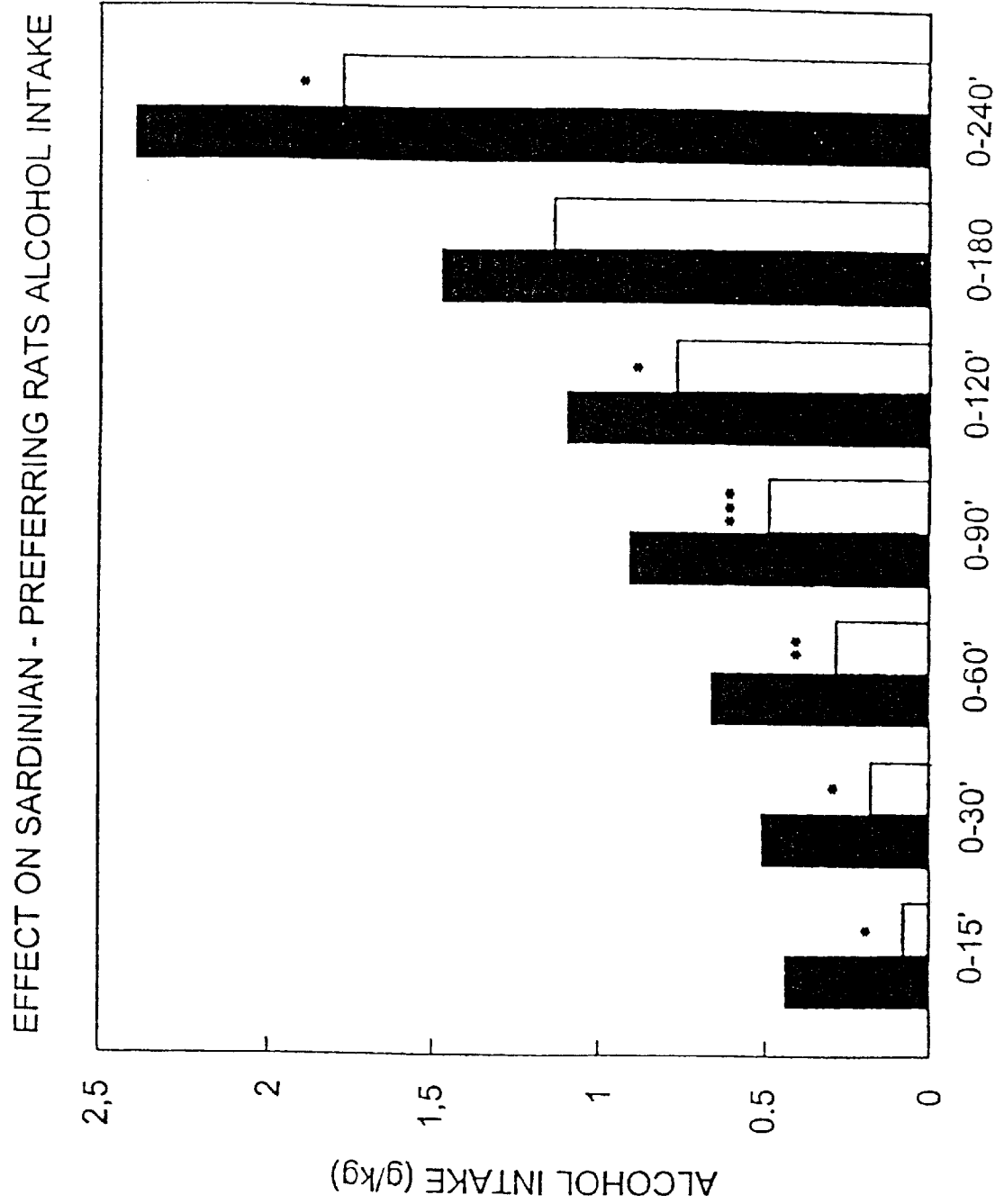

The collected data were statistically analyzed by using the T test of Student and were reported for 3 molecules, [Get—57], [Get—63], [Get—73], in FIGS. 1B, 1B and 2 both as far as the dosages and duration are concerned and compared with the results obtained with GHB (FIG. 1A).

The results obtained with compounds of formula (I) are decidedly better than those obtained with GHB.

What is claimed is:

1. Amide of formula (I)

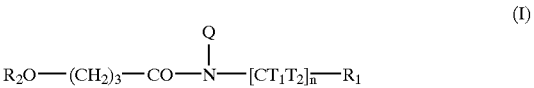

wherein the Amide is selected from:
compound 7) where Q=H, $T_1=T_2=H$, n=1, $R_1$=4-methylphenyl, and $R_2=CH_3$;
compound 8) where Q=H, $T_1=T_2=H$, $R_1$=3,5-dimethoxyphenyl, and $R_2=H$;
compound 10) where Q=H, $T_1=T_2=H$, n=1, $R_1$=phenyl, and $R_2=CH_3$;
compound 11) where Q=H, $T_1=T_2=H$, n=1, $R_1$=chlorophenyl, and $R_2=CH_3$;
compound 12) where Q=H, $T_1=T_2=H$, n=1, $R_1$=methylphenyl, and $R_2=CH_2CH_2$—;
compound 13 where Q=H, $T_1=T_2=H$, n=1, $R_1$=4-methylphenyl, and $R_2=CH_3CH_2CH_2$—;
compound 14) where Q=H, $T_1=T_2=H$, n=1, $R_1$-naphthyl, and $R_2=CH_3$;
compound 15) where Q=H, $T_1=T_2=H$, n=1, $R_1$=4-CF$_3$-phenyl, and $R_2=CH_3$; and
compound 16) where Q=CH$_3$, $T_1=T_2=H$, n=1, $R_1$=phenyl, and $R_2=H$.

2. The amide as claimed in claim 1, selected from compound 7) and compound 14).

* * * * *